United States Patent [19]
Cedrone

[11] Patent Number: 5,349,137
[45] Date of Patent: Sep. 20, 1994

[54] STERILIZABLE CABLE ASSEMBLIES
[75] Inventor: Alfredo Cedrone, Austin, Tex.
[73] Assignee: W. L. Gore & Associates, Inc., Newark, Del.
[21] Appl. No.: 63,387
[22] Filed: May 17, 1993
[51] Int. Cl.$^5$ .................................................. H02G 3/02
[52] U.S. Cl. .......................................... 174/76; 128/4; 174/74 R
[58] Field of Search ................ 174/28, 29, 68.1, 70 R, 174/70 L, 71 R, 71 L, 72 R, 72 C, 74 R, 74 A, 75 R, 75 L, 76, 77 R, 80, 82, 84 R, 88 R, 88 C, 110 R, 110 AR, 110 SR, 110 N, 110 PL, 110 E, 111, 113 R, 113 A, 120 R, 120 AR, 120 SR, 93, 92; 439/933, 936; 128/4, 6; 428/357, 364, 372, 375, 380, 382, 383, 389, 390, 394, 395, 396; 358/98

[56] References Cited
U.S. PATENT DOCUMENTS

| | | | |
|---|---|---|---|
| 4,015,072 | 3/1977 | Gillemot | 174/92 |
| 4,103,911 | 8/1978 | Giebal et al. | 174/77 R X |
| 4,105,481 | 8/1978 | Lofdahl | 156/79 |
| 4,341,205 | 7/1982 | Hosono | 128/6 |
| 4,425,476 | 1/1984 | Kyle | 174/152 GM |
| 4,593,970 | 6/1986 | Rhodes | 174/705 X |
| 4,657,337 | 4/1987 | Kyle | 174/152 GM X |
| 4,736,521 | 4/1988 | Dohya | 174/68.5 X |
| 4,878,485 | 11/1989 | Adair | 128/6 |
| 4,895,138 | 1/1990 | Yabe | 128/6 |
| 4,998,182 | 3/1991 | Krauter et al. | 128/4 X |
| 5,007,701 | 4/1991 | Roberts | 174/77 R |
| 5,043,223 | 8/1991 | Kumagai et al. | 428/432 |
| 5,110,387 | 5/1992 | Jasinski et al. | 156/222 |
| 5,155,303 | 10/1992 | Bensel, III et al. | 174/93 |
| 5,156,590 | 10/1992 | Vilmar | 604/4 |
| 5,217,808 | 6/1993 | Cobb | 428/375 X |
| 5,229,208 | 7/1993 | Tanaka | 428/375 X |
| 5,231,248 | 7/1993 | Shah | 174/76 |

FOREIGN PATENT DOCUMENTS

| | | | |
|---|---|---|---|
| 0467631 | 1/1992 | European Pat. Off. . | |
| 3441630 | 5/1985 | Fed. Rep. of Germany . | |
| 0837557 | 6/1960 | United Kingdom | 174/93 |
| 0889080 | 2/1962 | United Kingdom | 174/76 |
| 1269061 | 3/1972 | United Kingdom | 174/76 |
| 2107326 | 4/1983 | United Kingdom . | |
| WO9105282 | 4/1991 | World Int. Prop. O. . | |

Primary Examiner—Leo P. Picard
Assistant Examiner—Christopher Horgan
Attorney, Agent, or Firm—Gary A. Samuels

[57] ABSTRACT

A steam and liquid sterilizable assembly of electrical and optical fiber cables within a sealed polymer housing which features sealed joints and conductive traces between and through components. At least one optical fiber cable is sealed into a metal ferrule by an organic resin and the ferrule then sealed by soldering into a laminated, multilayer organic polymer disc or board. At least one electrical cable is soldered to one surface of the disc or board to a conductive trace which connects through and between the layers of the disc or board to a conductive electrical contact on the opposite surface of the disc or board. The disc or board with the optical and electrical contacts is embedded in a molded polymer housing. The assembly is useful in endoscopy applications.

8 Claims, 4 Drawing Sheets

STERILIZABLE CABLE ASSEMBLIES

FIELD OF THE INVENTION

This invention relates to a medical assembly of electrical conductors and optical fibers with a connector which can be sterilized for reuse by either steam or liquid.

BACKGROUND OF THE INVENTION

Assemblies which transmit electrical signals and/or light into and out of a human body are of increasing importance in medicine, particularly in the field of endoscopy. The cables of such assemblies must be flexible for easy manipulation both in and out of the body, the jacket of the cable must be tough to withstand wear, body fluids, and sterilization for reuse, and the cables must be anchored to signal and manipulation devices by connectors which are adequately sealed against steam and sterilizing liquids, such as glutaraldehyde and aqueous sterilant solutions, for example.

At present, almost no such assemblies are known, except for that described and disclosed in U.S. Pat. No. 5,231,248, filed Jul. 17, 1991, and assigned to the same assignee as this application. The above application, however, uses an entirely different method of assembly from this application.

SUMMARY OF THE INVENTION

The invention comprises a steam and liquid sterilizable assembly of electrical and optical fiber cables.

In one form of the invention, which is a cylindrical assembly, at least one optical fiber cable is sealed into a metal ferrule by an organic resin and the ferrule then sealed by solder into a laminated multilayer organic polymer disc. The disc has metal-plated apertures therethrough and conductive metal traces layer to layer. At least one electrical cable is soldered to one surface of the disc to a conductive trace which connects through and between the layers of the disc to a conductive electrical contact on the opposite surface of the disc. The disc, the at least one electrical cable, and the at least one optical fiber cable are imbedded then in a molded polymer housing which has no entry points for steam or liquids during sterilization. Dependent claims cover the configuration of the sealing resins, the disc, the housing, and the sealing properties of the assembly as a whole.

In an alternate form of the invention, the ferrule into which the optical fiber cable is sealed is separated from and not sealed by solder into the organic polymer board to which the electrical cables are connected. The electrical cables are terminated to a board of the same composition as a disc of the cylindrical form of the invention. The board may be thin and rectangular to be easily connected to an edge mount connector. The board and ferrule are together imbedded in a molded polymer housing of steam and liquid sterilizable resin to form a flat assembly.

DETAILED DESCRIPTION OF THE INVENTION

With reference to the figures, the invention is now described in detail to more distinctly and clearly delineate the various structures, methods, and materials pertaining to the invention.

Figure 1:
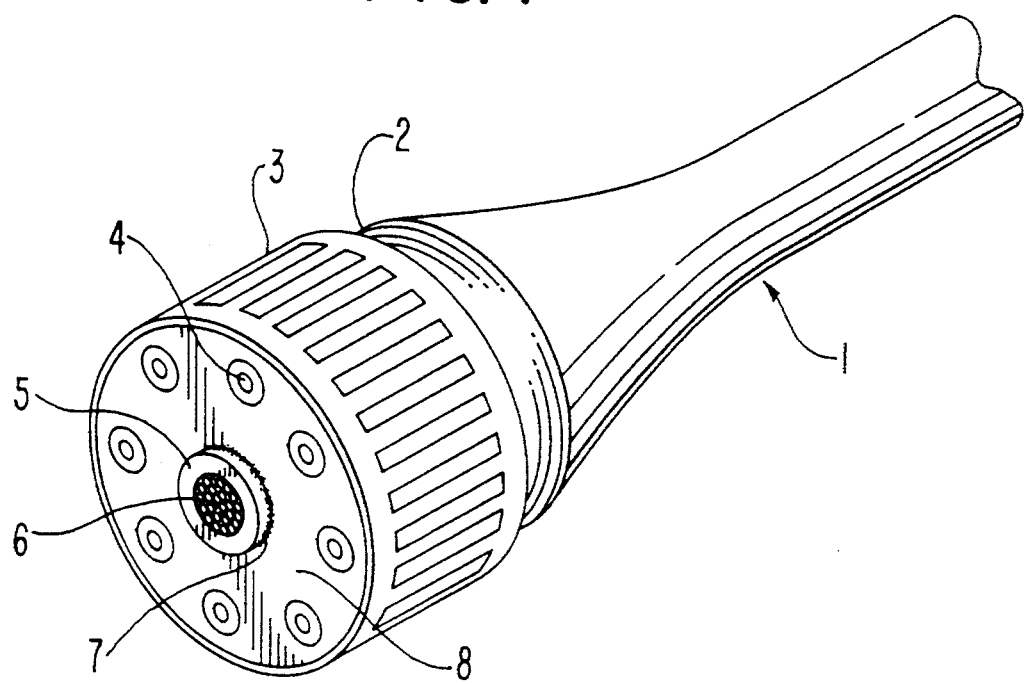
FIG. 1 is a perspective view of a cylindrical form of an assembly of the invention.

FIG. 1 shows in a perspective view the surface characteristics of an assembly of the invention of at least one optical fiber cable with at least one electrical cable in a cylindrical form of the assembly 1. The electrical and optical fiber cables are embodied in a single cable 11. On the face of the assembly, a ring of electrical contacts 4 surround the end of the optical fiber cable. The optical fiber cable comprises a multiplicity of optical fibers 6 cemented or sealed into a metal ferrule 5 by an epoxy resin, for example. After sealing, the optical fibers 6 are cut off at one end of ferrule 5 and the ends thereof polished to allow clear and accurate transmission of light. Ferrule 5 is soldered 7 into a metal-plated aperture in a laminated organic polymer disc 8. Electrical contacts 4 are affixed to the surface of disc 8 and connect via conductive traces through and between the layers making up the disc 8 to a metal-plated aperture on the other side of disc 8, where the electrical cable conductors of cable 11 are soldered into contact thereto. Molded polymer housing 3 is molded around disc 8, the end of cable 11, and its electrical cables and optical fiber cables in a sealed assembly resistant to sterilization by steam and organic liquids, such as glutaraldehyde or aqueous solutions of chemical sterilants. A groove 2 is conveniently molded into housing 3 to hold the end of a clamp which may be used to hold the assembly in contact with a mating connector.

A sexless connector, such as that of FIG. 1 having no male or female parts, has fewer cracks, crevaces, or other possible entry points for steam or liquids during sterilization. Typical materials for sterilization include steam under autoclave pressures and temperatures, ethylene oxide, and Cidex ® glutaraldehyde, for example.

Figure 2:
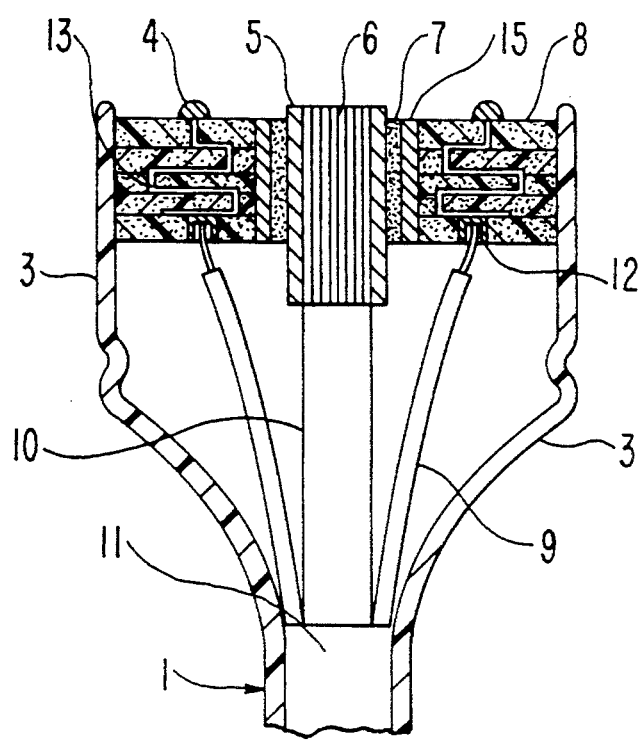
FIG. 2 is a cross-sectional view of the assembly of FIG. 1.

FIG. 2 describes in a cross-sectional view the interior parts of the assembly 1 of FIG. 1. Optical fibers 6 are sealed by an organic polymer resin, such as an epoxy resin, into metal ferrule 5. The ferrule is then soldered at 7 into an aperture in laminated organic polymer disc 8 which has been metal-plated 15 for this purpose. On the surface of disc 8 are electrical contacts (bumps) 4 affixed to its surface. Conductive traces 13 cement contacts 4 through and between the layers of disc 8 to metal-plated apertures 12 on the opposite surface of disc 8 from electrical contacts 4. The center conductors of electrical cables 9 are soldered into place in apertures 12. An organic polymer housing 3 is molded in sealing enclosure around disc 8, cables 9 and 10 and the end of cable 11 to form a sterilizable assembly thereof.

Figure 3:
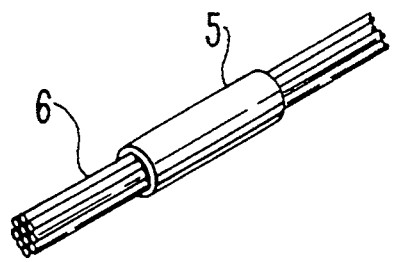
FIG. 3 is a perspective view of a bundle of optical fibers cemented into a metal ferrule.
Figure 4:
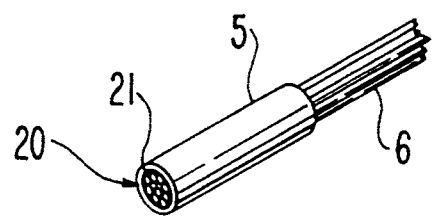
FIG. 4 is a perspective view of optical fibers cemented into a metal ferrule, the fibers cut off at one end of the ferrule and polished smooth.

FIG. 3 depicts a bundle containing a multiplicity of optical fibers 6 packed together as closely as possible inside a metal ferrule 5 into which they are cemented and sealed by an environmentally resistant polymer material, such as epoxy resin 21. In FIG. 4 is shown the optical fibers 6 cut off at one exit from ferrule 5 and the flat planar surface 20 created thereby polished to permit easy and accurate transmission of light for illumination of objects at the end of the cable, such as by an endoscope.

Figure 5:
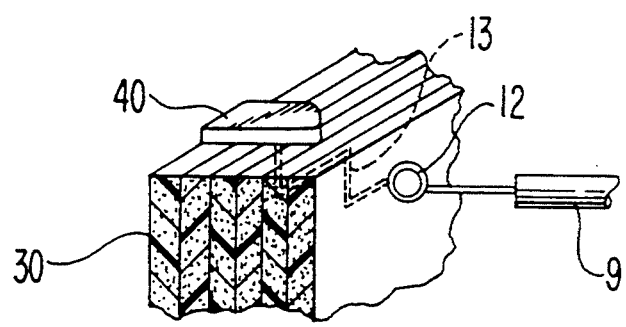
FIG. 5 is a perspective cross-sectional partial view of a section of laminated organic polymer board with conductive traces through and between the layers connecting an electrical contact on one surface to an electrical cable on the other surface thereof.

FIG. 5 is a partial perspective cross-sectional view of a laminated organic polymer board 30 which has an electrical contacts 40 affixed on one surface. Contact 40 is connected through and between the layers of board 30 by a conductive trace 13 which ends in a metal-plated aperture 12 on the surface of the board opposite to contact 40. The center conductor of an electrical cable 9 is soldered into aperture 12 to complete the electrical circuit. Board 30 is equivalent to disc 8 which may be cut in circular form from a segment of board 30. The layers of board 30 and disc 8 in FIG. 2, may be perpendicular to the surfaces bearing contacts 4 and metal-plated apertures 12 as an alternative to parallel. The opposite configuration of polymer layers also applies to board 8 of FIG. 5.

Figure 6:
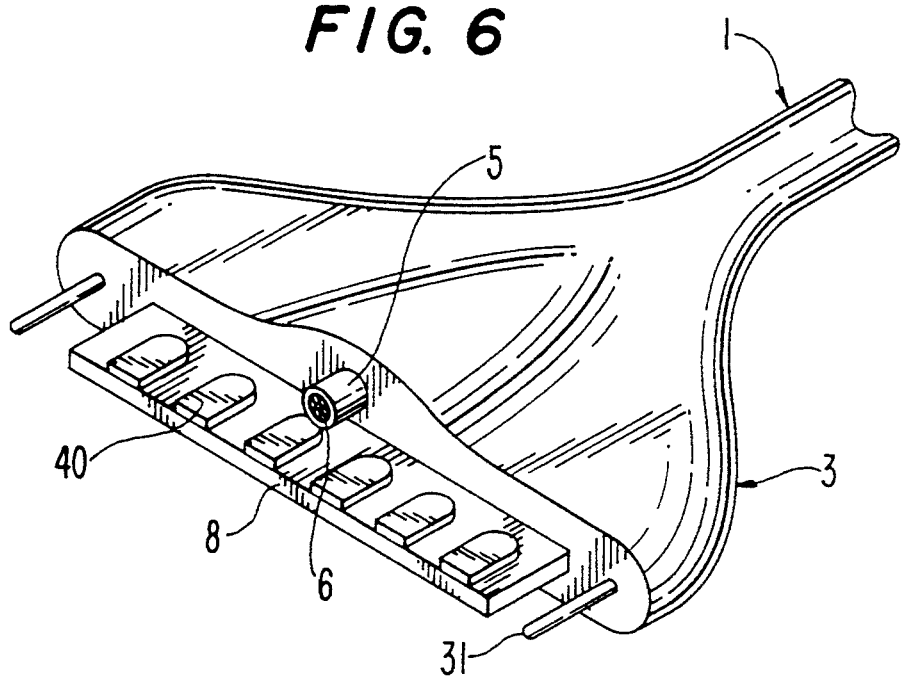
FIG. 6 is a flat cable version of an assembly of the invention for connection with an edge-contact connector for both electrical and optical contact.

FIG. 6 describes in a perspective view a flat form of an assembly of the invention. In this alternative, all the electrical cables are connected through flat board 8 and contacts 40 for mating with a card edge connector, such as those used on a computer circuit board. Guide pins 31 aid in easy mating of the assembly to the card edge connector. The optical cable to supply light parallels board 8 within housing 3 and the ferrule into which the optical fibers are sealed is imbedded in the polymer of housing 3 beside board 8, instead of being soldered into an aperture in board 8. The effect is the same, a sterilizable seal is provided in each form of the invention, with excellent resistance to steam and liquids.

As to materials of construction, the usual metals useful in electrical conductors, solders, conductive traces, and ferrules as are known in the electrical arts to be useful for those components are useful in this invention. The organic resins useful in sealing the optical fibers into the metal ferrule and to embed and surround conductor leads and cable wires include epoxy resins, such as Eccobond 45 clear, which can be obtained from Emerson and Cuming, Inc., of Woburn, Mass. The laminated multilayer organic polymer disc or board may be selected from expanded polytetrafluoroethylene and polytetrafluoroethylene both filled and unfilled, epoxy resin, epoxy resin filled with glass or mineral powder, chips, or fibers, polyimide, polyamide, polyamide imide, polycarbonate, and polysulfone, for example. The molded polymer housing material may be selected from an elastomeric steam and sterilizing liquid impervious silicone elastomers or fluoroelastomers, such as Fluorel ® elastomer (3M), Viton ® elastomer (DuPont), or Dail ® fluoroelastomer (Daikin KKK). The silicone elastomers useful for the housing most usefully have the recurring formula

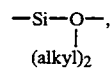

such as

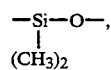

for example. This example is a Dow Corning "Silastic" Q7-4750 elastomer of uncured viscosity of about 700 centipoise at 25° C.

The assembly of the invention has the advantages of polymer sealing around its components and of use of conductive traces within an environmentally resistant laminated polymer board to minimize cracks and crevaces that might be attackable by steam or liquids during sterilization for reuse. Such assemblies are useful in the field of endoscopic surgical procedures for both illumination of a field and the carrying of electrical signals back and forth during the procedures.

I claim:

1. A steam and liquid sterilizable assembly of electrical and optical fiber cables comprising:
   (a) at least one optical fiber cable sealed into a metal ferrule by an organic resin, said ferrule being sealed by solder into an aperture in a
   (b) laminated, multilayer organic polymer disc, having metal-plated apertures therethrough and conductive metal traces layer to layer;
   (c) at least one electrical cable soldered to one surface of said disc to a conductive trace which connects through and between the layers of said disc to a conductive electrical contact on the opposite surface of said disc; and
   (d) wherein said at least one optical fiber cable, said at least one electrical cable, and said laminated, multilayer organic polymer disc are imbedded in a molded polymer housing which has no entry points for steam or liquids during sterilization.

2. A steam and liquid sterilizable assembly of electrical and optical fiber cables comprising:
   (a) at least one optical fiber cable sealed into a metal ferrule by an organic resin; (b) a laminated, multilayer organic polymer board, having metal-plated apertures and traces therethrough layer to layer;
   (c) at least one electrical cable soldered to one surface of said board to a conductive trace which connects through and between the layers of said board to a conductive electrical contact on the opposite surface of said board: and
   (d) wherein said at least one optical fiber cable sealed into a metal ferrule, said at least one electrical cable, and said laminated, multilayer organic board are imbedded in a molded polymer housing which has no entry points for steam or liquids during sterilization.

3. An assembly of claim 1 wherein said organic resin sealing said optical fibers into said ferrule, said multilayer organic polymer disc and said molding polymer of said housing resist attack by steam and sterilizing fluids.

4. An assembly of claims 1 or 2 wherein said organic resin sealing said optical fibers into said ferrule is selected from the group comprising of epoxy adhesives and epoxy sealants.

5. An assembly of claims 1 or 2 wherein said molded polymer housing is selected from the group consisting of silicone rubber and fluorinated hydrocarbon elastomer.

6. An assembly of claim 1 wherein said laminated, multilayer organic polymer disc is selected from the group consisting of expanded PTFE, spoxy resin filled with glass and polyimide.

7. An assembly of claim 2 wherein said organic resin sealing said optical fibers into said ferrule, said multilayer organic polymer board and said molding polymer of said housing resist attack by steam and sterilizing fluids.

8. An assembly of claim 2 wherein said laminated multilayer organic polymer board is selected from the group consisting of expanded PTFE, epoxy resin filled with glass and polyimide.

* * * * *